United States Patent [19]

Bose et al.

[11] Patent Number: 5,998,629
[45] Date of Patent: Dec. 7, 1999

[54] SYNTHESIS OF PYRAZOLOTRIAZOLE PHOTOGRAPHIC DYE FORMING COLOR COUPLERS AND INTERMEDIATES

[75] Inventors: Judith A. Bose, Webster; Ronald R. Valente, Rochester; Dino Aimino, Newark; Deborah D. DeMejo, Rochester, all of N.Y.

[73] Assignee: Eastman Kodak Company, Rochester, N.Y.

[21] Appl. No.: 09/204,444

[22] Filed: Dec. 2, 1998

[51] Int. Cl.$^6$ .................................................. C07D 249/18
[52] U.S. Cl. ............................................................ 548/262.4
[58] Field of Search ........................................... 548/262.4

[56] References Cited

U.S. PATENT DOCUMENTS

| | | | |
|---|---|---|---|
| 5,183,728 | 2/1993 | Romanet et al. | 430/386 |
| 5,457,210 | 10/1995 | Kim et al. | 548/262.4 |
| 5,565,572 | 10/1996 | Potenza et al. | 548/262.4 |
| 5,681,691 | 10/1997 | Bose et al. | 430/558 |

FOREIGN PATENT DOCUMENTS 0 779 543 A1   6/1997   European Pat. Off. .

*Primary Examiner*—Johann Richter
*Assistant Examiner*—Dominic Keating
*Attorney, Agent, or Firm*—J. Lanny Tucker

[57] ABSTRACT

Photographic pyrazolotriazole dye forming coupler compound or coupler intermediate compounds can be readily prepared by inducing an elimination-addition reaction between certain pyrazolotriazole compounds and aromatic amines in the presence of an inorganic base or formate. Yields and purity are high, and reaction time is reduced with the specific set of conditions and reactants, and environmental impact from waste is reduced. The resulting compounds can be used themselves as photographic dye forming couplers or further reacted to prepare useful coupler compounds for photographic use.

13 Claims, No Drawings

SYNTHESIS OF PYRAZOLOTRIAZOLE PHOTOGRAPHIC DYE FORMING COLOR COUPLERS AND INTERMEDIATES

COPENDING APPLICATION

Reference is made to copending and commonly assigned U.S. Ser. No. 09/203,459 filed on even date herewith by Valente and Bose and entitled "One-Pot Synthesis of Pyrazolotriazole Photographic Dye Forming Color Couplers and Coupler Intermediates."

FIELD OF THE INVENTION

This invention relates to a method of preparing pyrazolotriazole compounds that are useful as photographic dye forming couplers or as intermediates for the preparation of pyrazolotriazole photographic dye forming coupler compounds. In particular, it relates to a method of preparing certain 1-H-pyrazolo[5,1-c]-1,2,4-triazole compounds. This invention is useful in the photographic industry.

BACKGROUND OF THE INVENTION

Color photographic silver halide materials are used to provide color images with the use of certain dye forming compounds that are usually in the various photosensitive silver halide layers of the materials. These dye forming compounds are conventionally known as "dye forming couplers" and are reactive with suitable oxidized forms of color developing agents used during photoprocessing to provide the desired dye images. Since most of such silver halide materials (such as color negative films and color papers) provide images based on what is known in the art as "subtractive color mixing", they typically include dye forming couplers that will provide cyan, yellow and magenta dyes in the appropriate photosensitive layers.

Pyrazolotriazoles have been known to be useful photographic magenta dye forming couplers for some time, and various processes are known for preparing them, all of which usually include various chemical reactions taken in specific order. Such processes add functionality that defines the desired dye forming coupler early in the synthesis. These processes result in the lack of generality of the process and the need to make different intermediates for different dye forming coupler end products.

It is well known in the art [for example, U.S. Pat. No. 5,183,728 (Romanet et al), U.S. Pat. No, 5,457,210 (Kim et al) and U.S. Pat. No. 5,565,572 (Potenza et al)] that coupler precursors defined by Formula I below can be converted to coupler intermediates defined by Formula II (wherein $R_3$ is an alkyl group and $R_4$ is hydrogen) by reacting a Formula I compound with a primary aliphatic amine in refluxing tetrahydrofuran (THF).

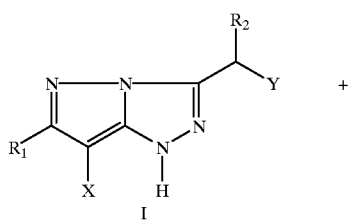

I

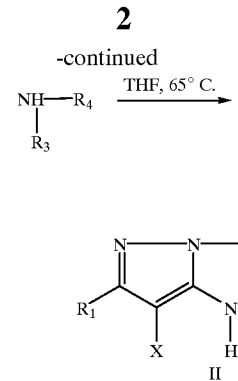

II

This reaction works well if $R_3$ is an alkyl group and $R_4$ is hydrogen, but it does not work well (i.e. resulting in long reaction times and/or low chemical yields) if either $R_3$ or $R_4$ is an aromatic group.

It is also known from the noted Kim et al and Potenza et al patents that this same transformation can be affected by adding triethylamine to the reaction mixture.

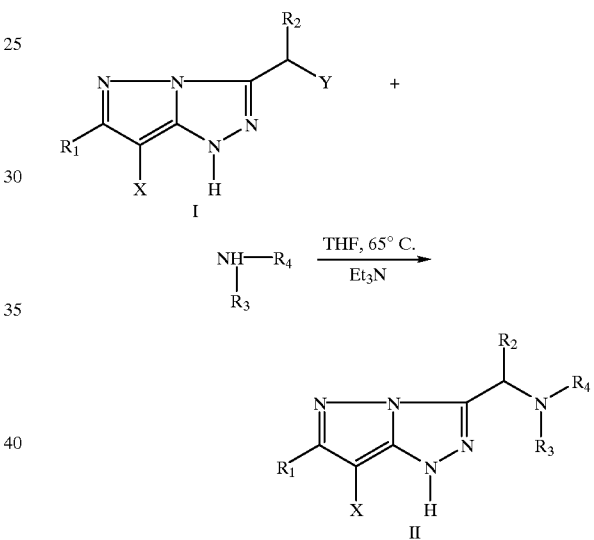

While this reaction works well if $R_3$ is an alkyl group and $R_4$ is hydrogen, if either $R_3$ or $R_4$ is an aromatic group, the results (i.e. chemical yield, reaction times, and product purity) are variable and substrate dependent. Additionally, disposal of reaction process waste material containing an organic base like triethylamine presents a more serious environmental problem.

There remains a need in the photographic industry for a synthetic method for preparing dye forming coupler intermediates of the pyrazolotriazole type that can be carried out with reactants containing aromatic groups with high yield, high purity and shortened reaction time, while the environmental impact of waste disposal is minimized.

SUMMARY OF THE INVENTION

These problems are overcome with a method for preparing a pyrazolotriazole photographic dye forming coupler compound or coupler intermediate compound comprising inducing an elimination-addition reaction between an aromatic amine and a compound having Structure I in the presence of an inorganic base, a formate salt or both,

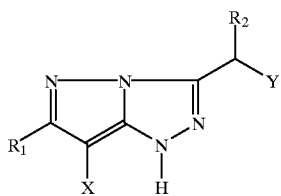

I

Wherein $R_1$ is an alkyl, aryl, alkoxy, aryloxy or amido group, $R_2$ is hydrogen or an alkyl or aryl group, X is hydrogen or a coupling-off group or a precursor thereof, and Y is a leaving group that is capable of being replaced by an elimination-addition reaction.

The present invention also provides a method of preparing a pyrazolotriazole photographic dye forming coupler compound comprising:

A) inducing an elimination-addition reaction between an aromatic amine with a compound having Structure I in the presence of an inorganic base, a formate salt or both, and B) further reacting the product obtained in step A.

The present invention is advantageous because it provides a dye forming coupler compound or coupler intermediate compound in high yield and purity using a synthesis that can be carried out using an aromatic amine reactant, and that has minimal environmental impact. These advantages are unexpectedly achieved with the use of an inorganic base or formate salt in an aqueous or polar organic solvent reaction medium.

The present invention can be used to prepare pyrazolotriazole dye forming coupler compounds that are reactive with oxidized photographic color developing agents to provide dyes. Such coupler compounds may be useful in various photographic silver halide materials, or in photochemical processing solutions that are useful for providing colored images from such materials. Alternatively, the compounds prepared using the present invention may be further reacted as one skilled in the art would readily understand, to add ballast groups, coupling off or other reactive groups. The resulting compounds can then be used in any suitable manner.

DETAILED DESCRIPTION OF THE INVENTION

The present invention is a method for converting compounds of Structure I to compounds of Structure II in reaction media that include an inorganic base (defined below) or a formate salt while using the reaction conditions described below. Upon completion of the reaction, the resulting salts can be removed by filtration or by adding a water-immiscible organic solvent and washing with water or a mildly acidic solution. Any organic solvent remaining in reaction medium can be removed by distillation.

The general reaction scheme of the invention is shown as follows:

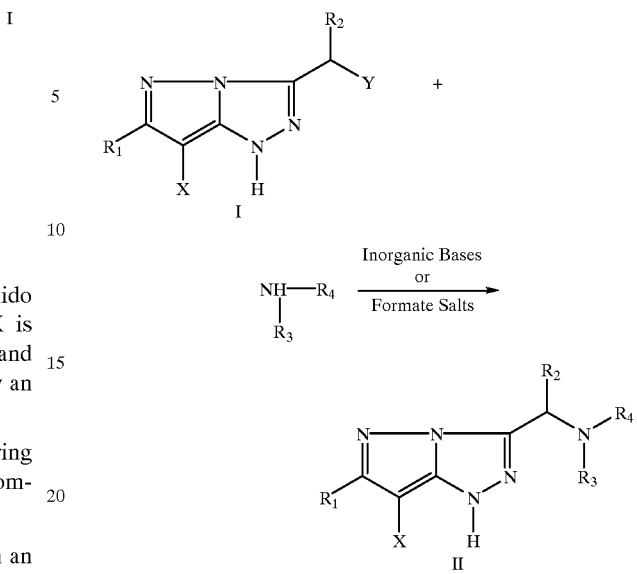

In Structure I, $R_1$ can be, but is not limited to, any of the groups conventionally found in this position on corresponding photographic dye forming couplers or precursors thereof. For example, useful $R_1$ groups include, but are not limited to, substituted or unsubstituted alkyl having from 1 to 12 carbon atoms (for example, methyl, ethyl, methoxymethyl, isopropyl, t-butyl, n-pentyl, n-hexyl, decyl, dodecyl, benzyl and phenethyl), substituted or unsubstituted cycloalkyl having 5 to 12 carbon atoms in the ring (or combination of rings, such as cyclopentyl, cyclohexyl and 4-methylcyclohexyl), substituted or unsubstituted alkoxy having 1 to 12 carbon atoms (such as methoxy, 2-ethoxy, isopropoxy, methoxymethoxy and benzoxy), substituted or unsubstituted alkyloxysulfonyl (wherein the alkyl portion has 1 to 12 carbon atoms as defined above), substituted or unsubstituted alkylsulfonyl (wherein the alkyl portion has 1 to 12 carbon atoms as defined above), substituted or unsubstituted aryl having 6 to 12 carbon atoms in the aromatic ring (or combination of rings, such as phenyl, p-methylphenyl, 3-methoxyphenyl, naphthyl, tolyl, halophenyl groups, nitrophenyl groups, aminophenyl groups, carboxyphenyl groups, methoxycarbonylphenyl groups, hydroxyphenyl groups and ethoxyphenyl groups), substituted or unsubstituted aryloxy having 6 to 12 carbon atoms in the aromatic ring (or combination of rings, such as phenoxy, p-methylphenoxy, halophenoxy groups, aminophenoxy groups and alkylphenoxy groups), substituted or unsubstituted aryloxysulfonyl wherein the aryl portion is as defined above, and substituted or unsubstituted arylsulfonyl wherein the aryl portion is as defined above.

$R_1$ can also be a substituted or unsubstituted acyl group (such as acetyl or —OCOCH$_2$CH$_3$), substituted or unsubstituted amino (including alkyl- and arylamines), amido (such as methamido, 2-ethylamido and t-butylamido), substituted or unsubstituted alkylthio wherein the alkyl portion has 1 to 12 carbon atoms (as defined above), substituted or unsubstituted arylthio wherein the aryl portion has from 6 to 12 carbon atoms in the ring structure (as defined above), or a substituted or unsubstituted heterocyclyl having from 5 to 12 carbon, nitrogen, oxygen or sulfur atoms in the heterocyclic ring (or combination of rings). Useful heterocyclyl groups include, but are not limited to, pyridyl, pyrimidyl, pyrazolyl, pyrrolyl, oxazoyl, thiazolyl, furanyl and thiophenyl.

In preferred embodiments, $R_1$ is a substituted or unsubstituted alkyl, substituted or unsubstituted aryl, amido, substituted or unsubstituted acyl group, substituted or unsubstituted alkoxy or substituted or unsubstituted aryloxy group as defined above (for example, methyl, ethyl, isopropyl, t-butyl, methoxy, ethoxy, phenyl, phenoxy, a methylphenyl group, a chlorophenyl group, a nitrophenyl group, a methoxyphenyl group and t-butylamido). Amido and acyl are the least preferred of such groups. Most preferably, $R_1$ is a substituted or unsubstituted alkyl group, such as substituted or unsubstituted methyl, ethyl, isopropyl and t-butyl groups, or phenoxy group.

$R_2$ is hydrogen, or a substituted or unsubstituted alkyl, substituted or unsubstituted aryl or substituted or unsubstituted heterocyclyl, as defined above for $R_1$ (obviously, $R_1$ and $R_2$ can be different groups). Preferably, $R_2$ is a substituted or unsubstituted aryl group (such as phenyl, chlorophenyl groups, methylphenyl groups, methoxyphenyl groups, nitrophenyl groups), or a substituted or unsubstituted alkyl group having 1 to 4 carbon atoms (such as methyl, ethyl, isopropyl, isobutyl and t-butyl groups). More preferably, $R_2$ is a substituted or unsubstituted phenyl group (such as p-nitrophenyl) or a substituted or unsubstituted alkyl group (such as a methyl, ethyl, or t-butyl group). Substituted or unsubstituted methyl, ethyl and phenyl groups are the most preferred $R_2$ groups.

Also within Structure I, X is hydrogen or a coupling off group or a precursor thereof. Such coupling off groups are well known in the photographic art as groups that can be replaced by oxidized color developing agent during photographic processing (that is, color development). Such groups can determine the chemical equivalency of a coupler, that is whether it is a 2-equivalent or a 4-equivalent coupler, or modify the reactivity of the coupler. The presence of hydrogen at the coupling site ("X") provides a 4-equivalent coupler, and the presence of the coupling off group usually provides a 2-equivalent coupler.

Representative coupling off groups (or precursors thereof) include, but are not limited to, halo (such as chloro or bromo), substituted or unsubstituted alkoxy having 1 to 12 carbon atoms (as defined above for $R_1$), substituted or unsubstituted aryloxy having 6 to 12 carbon atoms in the aromatic ring (or combination of rings, as defined above for $R_1$), substituted or unsubstituted hetero-oxy (that is a heterocyclyl attached through an oxy group) having from 5 carbon and heteroatoms in the heterocyclyl ring(s), substituted or unsubstituted alkylthio wherein the alkyl portion has from 1 to 12 carbon atoms as defined above for $R_1$, arylthio wherein the aryl portion has from 6 to 12 carbon atoms as defined above for $R_1$, heterocyclyl as defined above for $R_1$, sulfonyloxy, acyloxy, acyl, sulfonamido, mercaptopropionic acid, phosphonyloxy and arylazo.

Preferably, X is hydrogen, halo, phenoxy, a substituted or unsubstituted alkylthio group (such as methylthio or carboethoxyethylthio) or a substituted or unsubstituted arylthio group (such as phenylthio), and most preferably, X is hydrogen, chloro, phenoxy or carboethoxyethylthio.

Y is a leaving group that is capable of being replaced in an elimination-addition reaction. Such groups include, but are not limited to, halo, hydroxy, substituted or unsubstituted aryloxy having 6 to 12 carbon atoms in the aryl portion (as defined above for $R_1$), substituted or unsubstituted alkoxy (as defined above for $R_1$) substituted or unsubstituted acyloxy (such as acetyloxy and —OCOalkyl$_{C2-C8}$), substituted or unsubstituted alkylsulfonyloxy or arylsulfonyloxy (as defined above for $R_1$). Preferred Y groups include, but are not limited to, halo, and substituted or unsubstituted aryloxy, acyloxy and alkoxy groups. More preferably, Y is halo (such as chloro), p-nitrophenoxy or an acetoxy group. Addition-elimination reactions are described for coupler synthesis in U.S. Pat. No. 5,183,728 (noted above).

Unless otherwise specifically stated, substituent groups which may be substituted on compounds of Structures I or II or the aromatic amines described herein include any groups, whether substituted or unsubstituted, that do not destroy properties necessary for photographic utility. When the term "group" is applied to the identification of a substituent containing a substitutable hydrogen, it is intended to encompass not only the substituent's unsubstituted form, but also its form that is further substituted with any group or groups as herein mentioned. Suitably, the group may be halo or may be bonded to the remainder of the molecule by an atom of carbon, silicon, oxygen, nitrogen, phosphorous, or sulfur. The substituent may be, for example, halo (such as chloro, bromo or fluoro), nitro, hydroxyl, cyano, carboxyl, or groups which may be further substituted, such as alkyl, including straight or branched chain alkyl [such as methyl, trifluoromethyl, ethyl, t-butyl, 3-(2,4-di-t-pentylphenoxy) propyl, and tetradecyl], alkenyl (such as ethylene and 2-butene), alkoxy [such as methoxy, ethoxy, propoxy, butoxy, 2-methylphenoxy, sec-butoxy, hexyloxy, 2-ethylhexyloxy, tetradecyloxy, 2-(2,4-di-t-pentylphenoxy) ethoxy and 2-dodecyloxyethoxy], aryl (such as phenyl, 4-t-butylphenyl,2,4,6-trimethylphenyl and naphthyl), aryloxy (such as phenoxy, 2-methylphenoxy, α- or β-naphthyloxy and 4-tolyloxy), carbonamido [such as acetamido, benzamido, butyramido and tetradecanamido, α-(2,4-di-t-pentyl-phenoxy)acetamido, α-(2,4-di-t-pentylphenoxy)butyramido, α-(3-pentadecylphenoxy)-hexanamido and α-(4-hydroxy-3-t-butylphenoxy)-tetradecanamido], 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonylamino, p-dodecyl-phenylcarbonylamino, p-toluylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-duphenylureido, N-phenyl-N-p-toluylureido, N-(m-hexadecylphenyl)ureido, N,N-(2,5-di-t-pentylphenyl)-N'-ethylureido, and t-butylcarbonamido, sulfonamido (such as methylsulfonamido, benzenesulfonamido, p-toluylsulfonamido, p-dodecylbezenesulfonamido, N-methyltetradecylsulfonamido, N,N-dipropylsulfamoylamino and hexadecylsulfonamido), sulfamoyl {such as N-methylsulfamoyl, N-ethylsulfamoyl, N,N-dipropylsulfamoyl, N-hexadecylsulfamoyl and N,N-dimethylsulfamoyl), N-[3-(dodecylocy)propyl]sulfamoyl, N-[4-(2,4-di-t-pentylphenoxy)butyl]sulfamoyl, N-methyl-N-tetradecylsulfamoyl, and N-dodecylsulfamoyl}, carbamoyl {such as N-methylcarbamoyl, N,N-dibutylcarbamoyl, N-octadecylcarbamoyl, N-[4-(2,4-di-t-pentylphenoxy) butyl]carbamoyl, N-methyl-N-tetradecylcarbamoyl, and N,N-dioctylcarbamoyl}, acyl [such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl], sulfonyl (such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl and p-toluylsulfonyl), sulfonyloxy (such as dodecylsulfonyloxy and hexadecylsulfonyloxy), sulfinyl (such as methylsulfinyl, octylsulfinyl, 2-ethylhexylsulfinyl, dodecylsulfinyl, hexadecylsulfinyl, phenylsulfinyl, 4-nonylphenylsulfinyl and p-toluylsulfinyl), thio [such as ethylthio, octylthio, benzylthio, tetradecylthio, 2-(2,4-di-t-pentylphenoxy) ethylthio, phenylthio, 2-butoxy-5-t-octylphenylthio and p-tolylthio], acyloxy (such as acetyloxy, benzoyloxy, octadecanoyloxy, p-dodecylamidobenzoyloxy, N-phenylcarbamoyloxy, N-ethylcarbamoyloxy, and cyclohexylcarbonyloxy), amine (such as phenylanilino, 2-chloroanilino, diethylamine or dodecylamine), imino [such as 1-(N-phenylimido)ethyl, N-succinimido or 3-benzylhydantoinyl], phosphate (such as dimethylphosphate and ethylbutylphosphate), phosphite (such as diethyl and dihexylphosphite), a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl, quaternary ammonium, such as triethylammonium, and silyloxy (such as trimethylsilyloxy).

If desired, the substituents may themselves be further substituted one or more times with any of the described substituent groups. The particular substituents used may be selected by those skilled in the art to attain the desired photographic properties for a specific application and can include, for example, hydrophobic groups, solubilizing groups, blocking groups, releasing or releasable groups, etc. Generally, the above groups and substituents thereof may include those having up to 48 carbon atoms, typically I to 36 carbon atoms and usually less than 24 carbon atoms, but greater numbers are possible depending on the particular substituents selected.

Some representative compounds of Structure I are listed in TABLE I below:

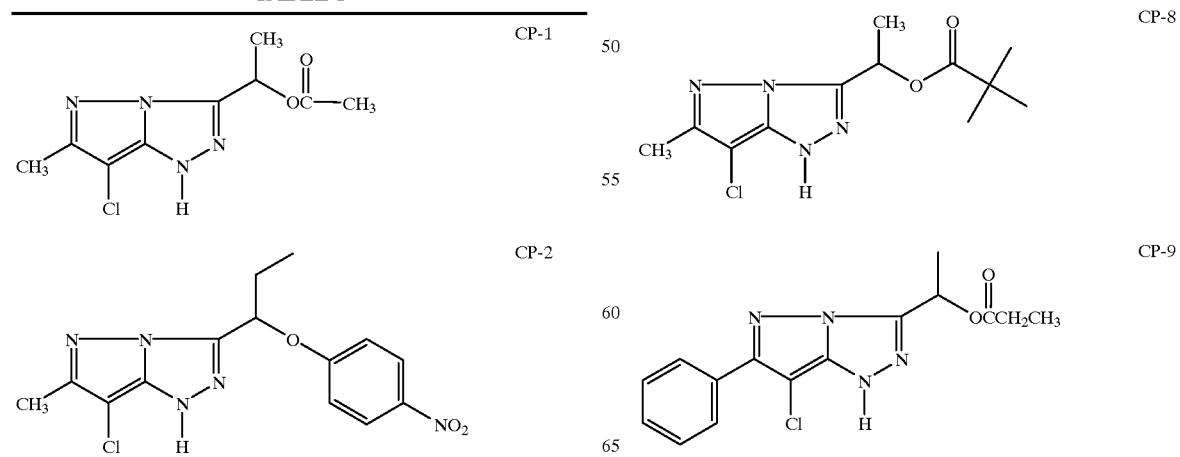

TABLE I-continued

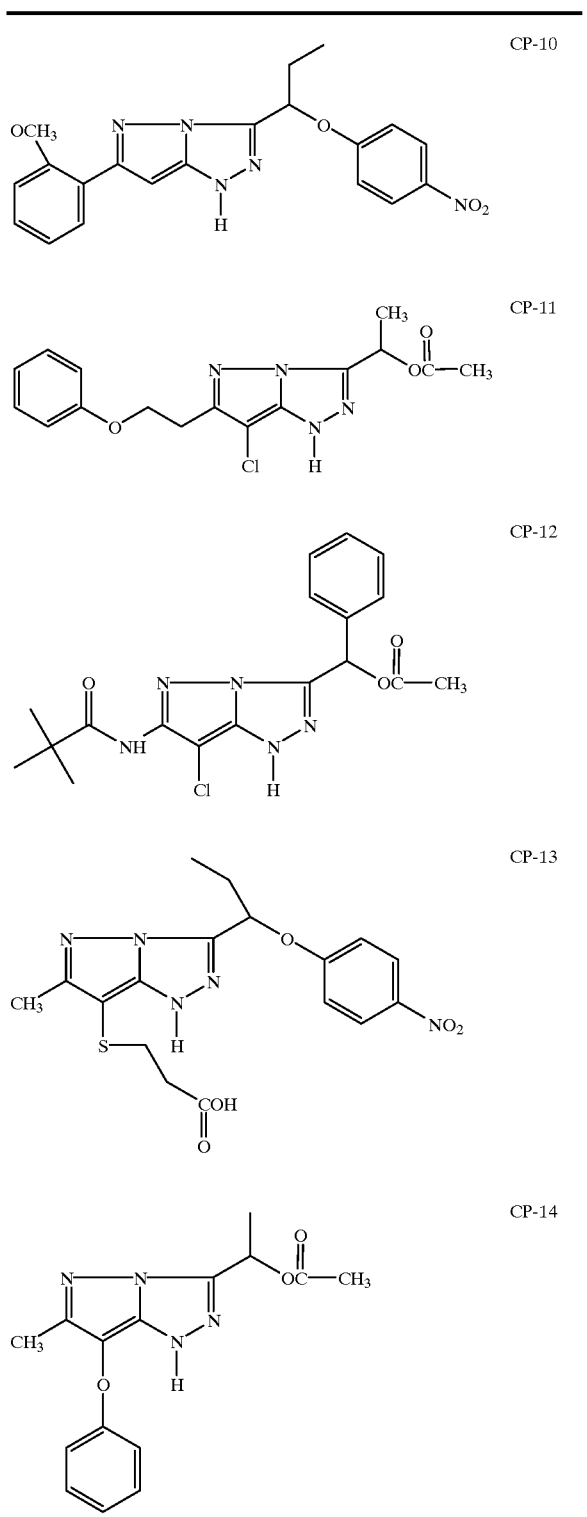

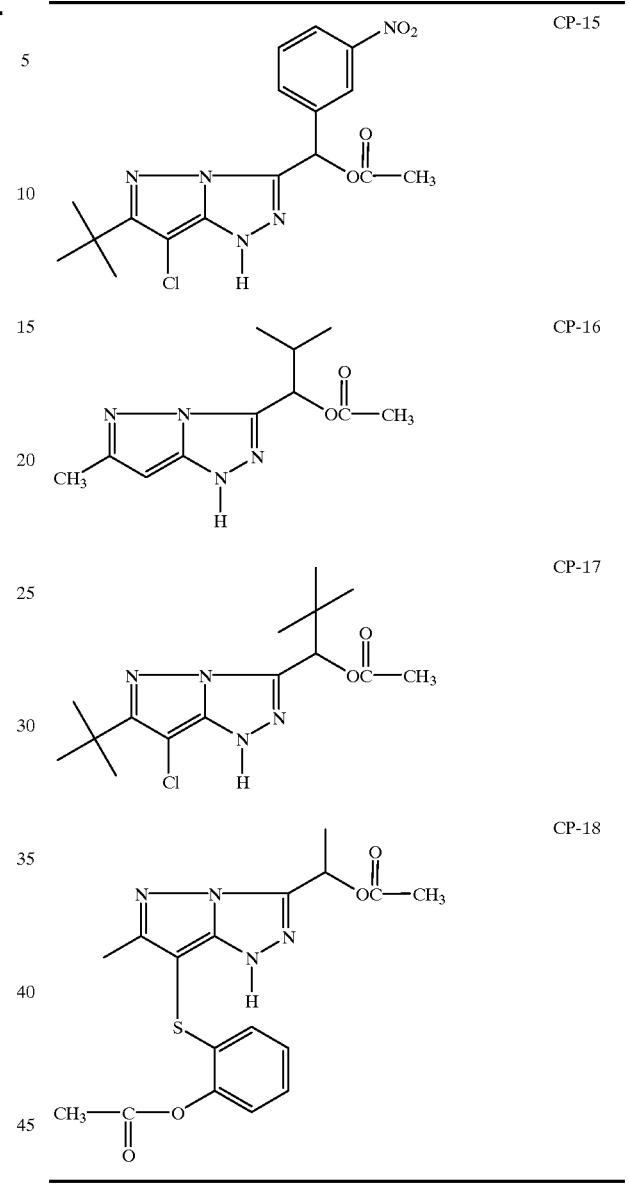

The compounds represented by Structure I can be provided for the practice of this invention by preparing them from conventional starting materials and using known reaction conditions (for example, as described in the Potenza et al and Kim et al patents noted above).

Aromatic amines used in the practice of the invention can be represented by $NH(R_3)R_4$ wherein at least one of $R_3$ and $R_4$ is a substituted or unsubstituted aromatic group (either carbocyclyl or heterocyclyl) having 5 to 12 atoms in its ring system (single or multiple fused rings), and the other is hydrogen, a substituted or unsubstituted alkyl group having 1 to 12 carbon atoms (as defined above for $R_1$), or a substituted or unsubstituted aryl group (as defined above for $R_1$). Preferably, one of $R_3$ and $R_4$ is hydrogen or a substituted or unsubstituted alkyl group, and more preferably, one of them is hydrogen while the other is a substituted or unsubstituted aryl group. Particularly useful aromatic groups include phenyl or other 6 to 10-membered aryl groups having large ballast groups as a substituent. Such ballast groups generally have at least 12 carbon, oxygen, sulfur and nitrogen atoms in the chain.

Useful aryl groups (carbocyclic) include those defined above for $R_1$. Representative aryl groups include, but are not limited to, phenyl, alkylphenyl groups, bromophenyl groups, carboxyphenyl groups, cyanophenyl groups, acetylphenyl groups, alkoxyphenyl groups, and others that would be readily apparent to one skilled in the art. The preferred aryl groups are phenyl and substituted phenyl groups. Useful aromatic heterocyclyl groups have 5 to 12 carbon, nitrogen, oxygen or sulfur atoms in the aromatic ring (or combination of rings). Representative aromatic heterocyclyl groups include, but are not limited to, pyridinyl and isoquinolinyl.

Some useful aromatic amines (for example AS-6, AS-7, AS-10, AS-11, AS-12, AS-13 and AS-14 identified below) can be purchased from a number of commercial sources (for example, Aldrich Chemical Co.), or by synthesizing them using conventional starting materials and reaction conditions (see for example EP-A-0 779,543 of Bose et al). In general, they can be prepared by reduction of a corresponding nitro-substituted aromatic compound. The precursor nitro-substituted aromatic compounds can be obtained generally from various commercial sources.

Some typical amine reactants are listed below in TABLE II.

TABLE II

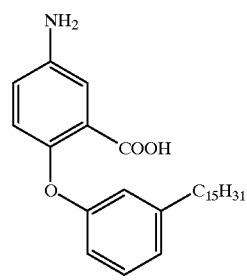
AS-1

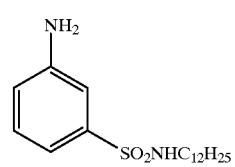
AS-2

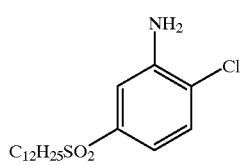
AS-3

TABLE II-continued

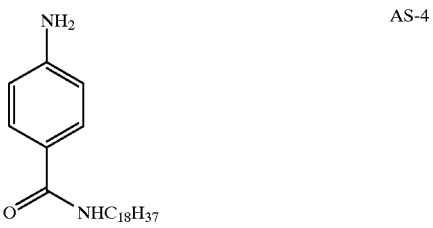
AS-4

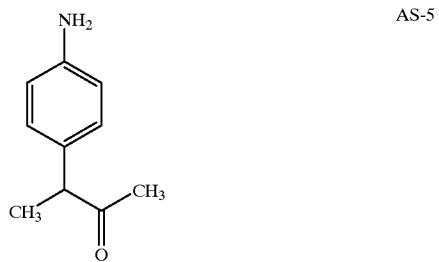
AS-5

AS-6

AS-7

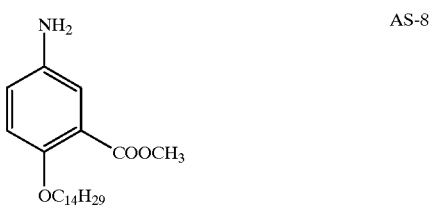
AS-8

AS-9

AS-10

TABLE II-continued
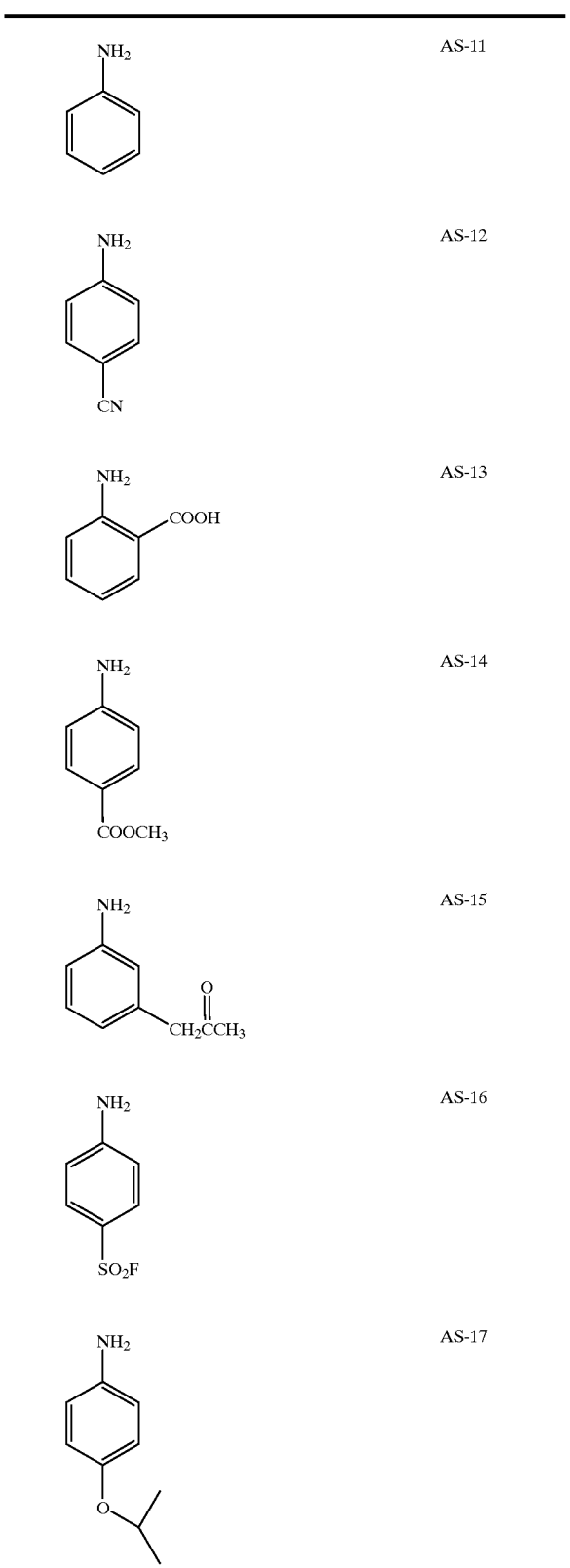
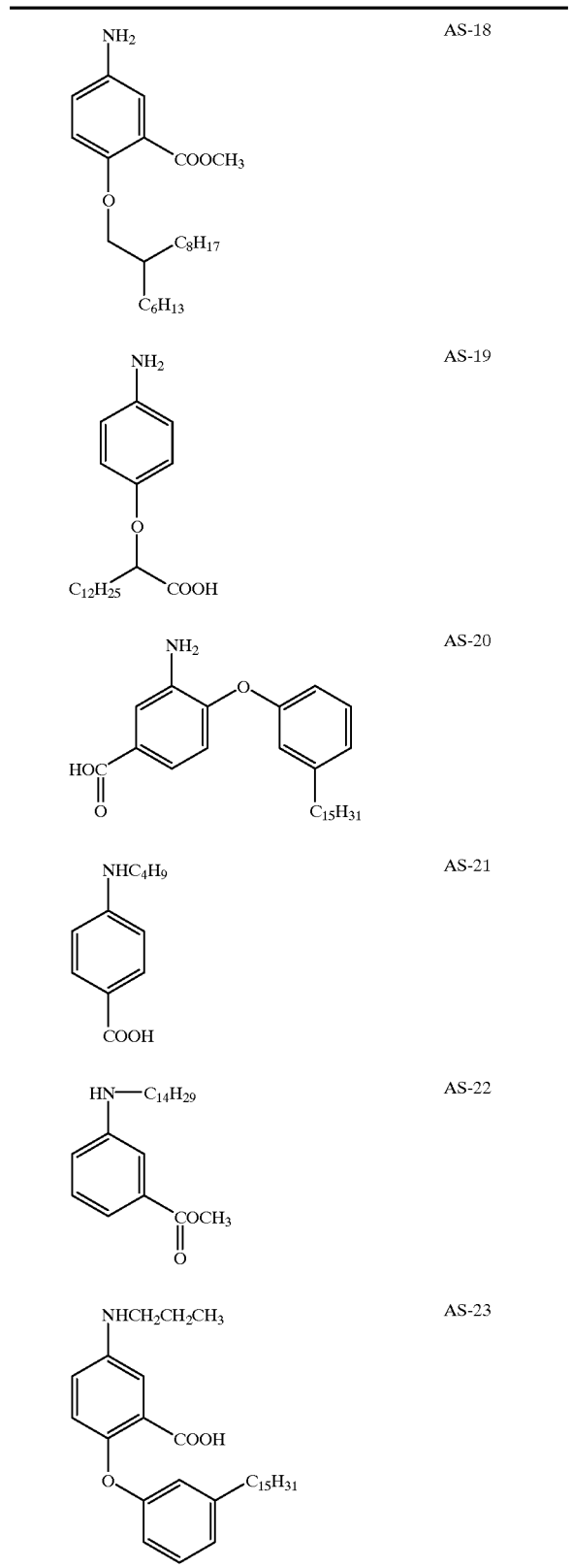

TABLE II-continued

AS-24 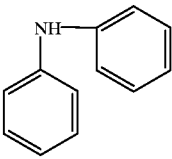

AS-25 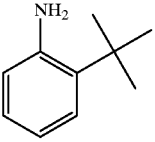

AS-26 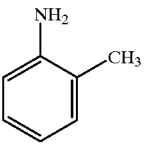

AS-27 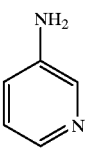

AS-28 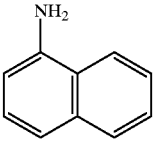

AS-29 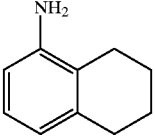

AS-30 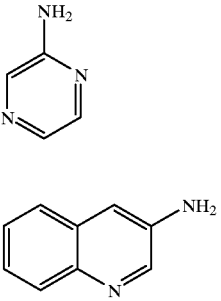

AS-31 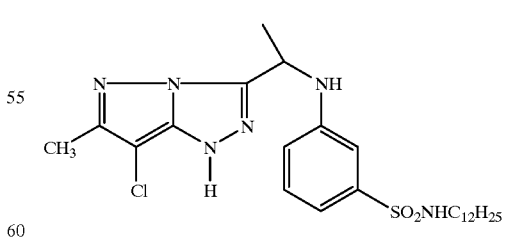

TABLE II-continued

AS-32 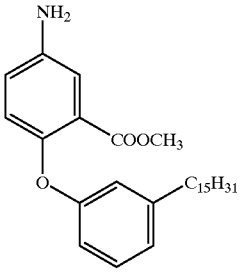

As noted above, the pyrazolotriazole compounds prepared using the present invention can be used as photographic dye forming coupler compounds without further modification. Alternatively, they can be used as "intermediates" that are further reacted to provide the desired photographic dye forming coupler compounds of interest. Examples of compounds of Structure II obtained using the method of this invention are listed below in TABLE III.

TABLE III

P-1 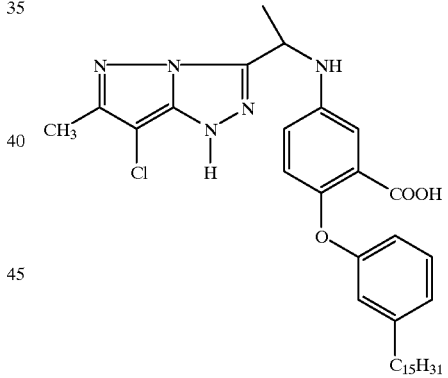

P-2

TABLE III-continued
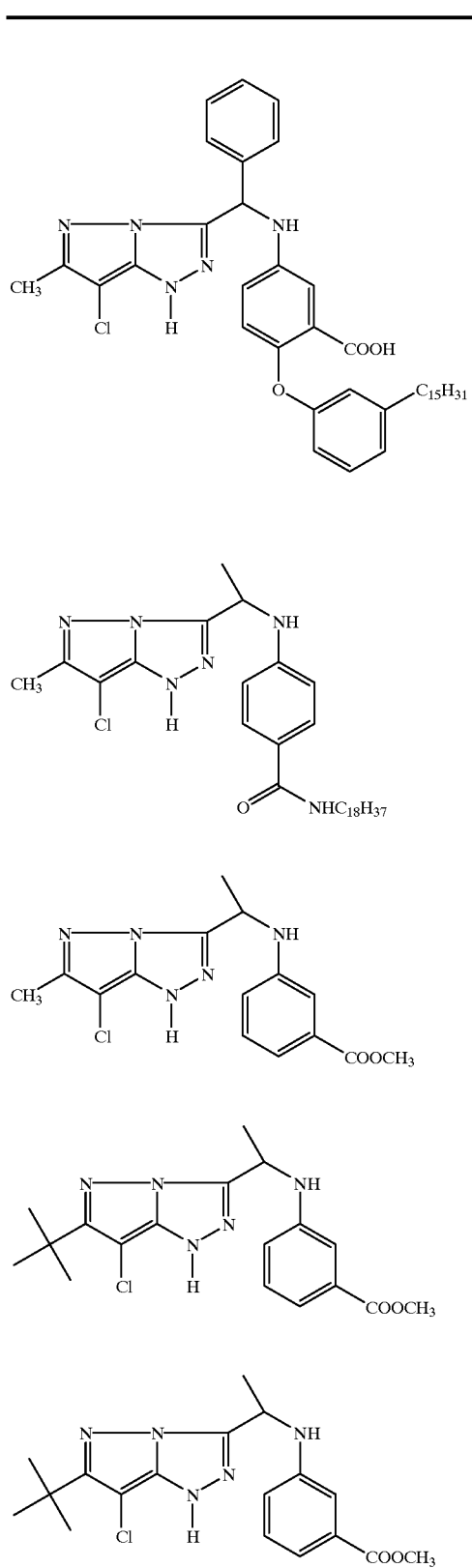
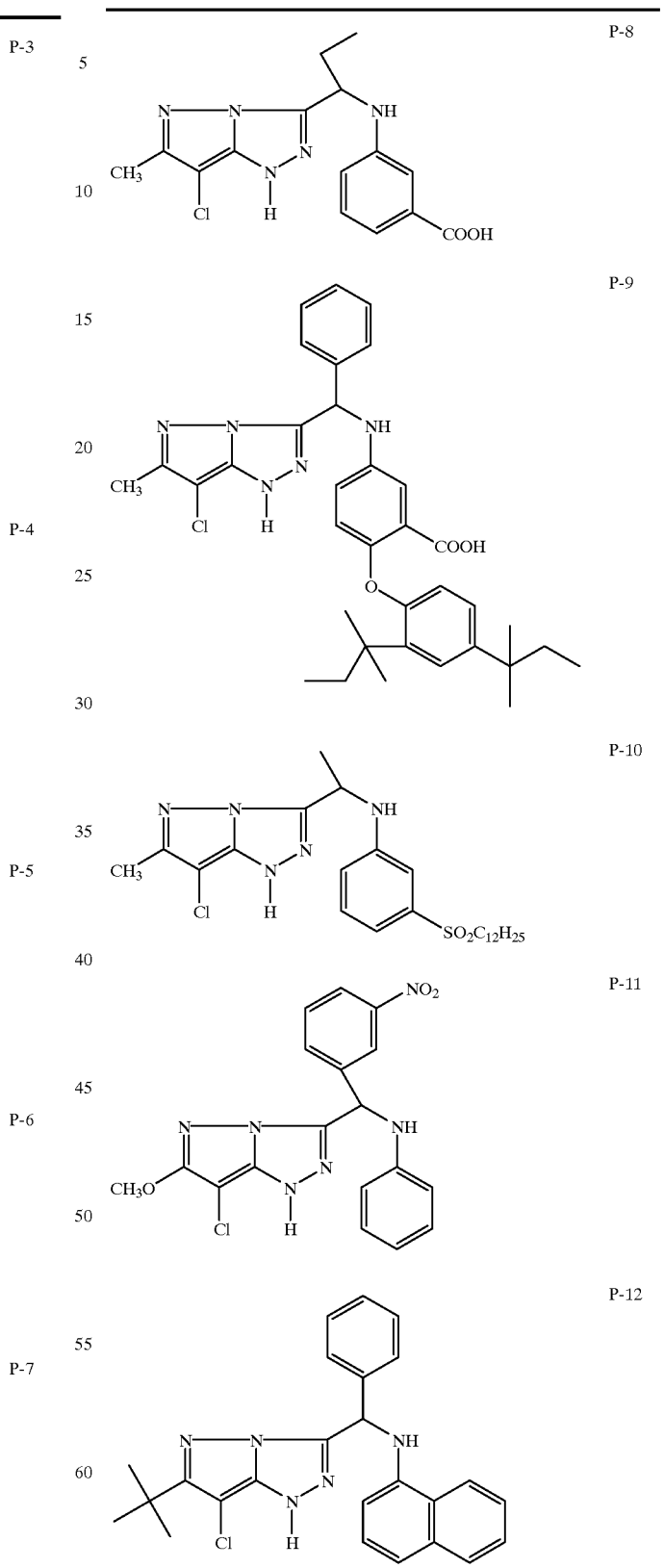

TABLE III-continued

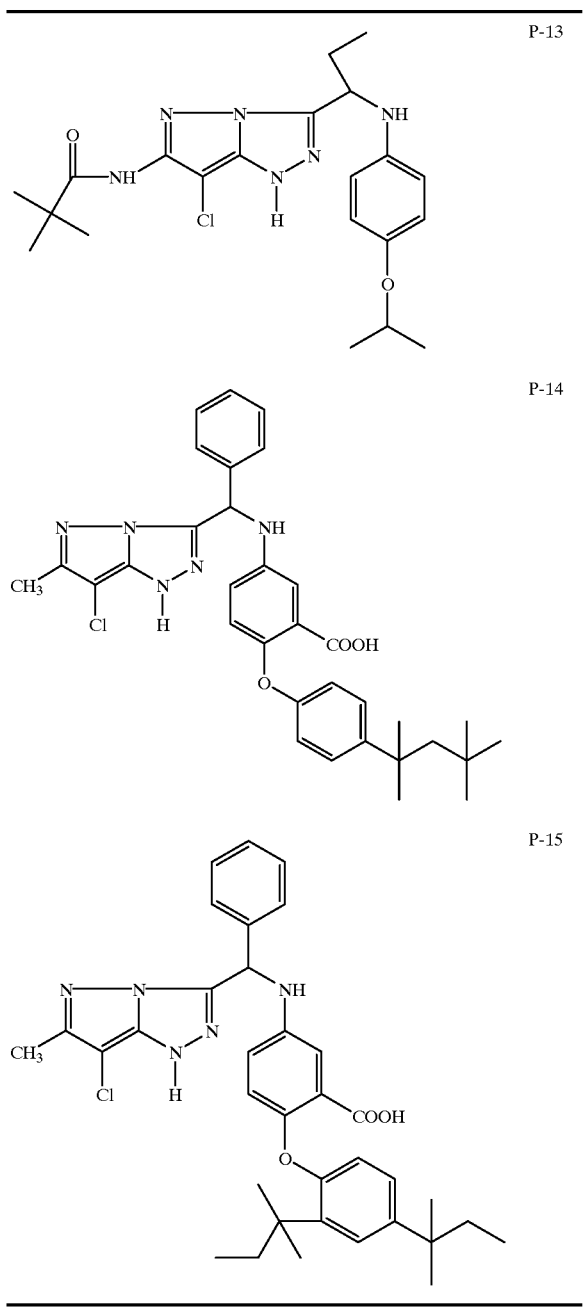

The general conditions for preparing the compounds of Structure II include a reaction temperature that is at least 25° C., preferably at least 35° C., and more preferably at least 40° C. The reaction temperature can be generally up to 65° C., preferably up to 55° C., and more preferably up to 50° C.

The reaction media can be aqueous, or composed of one or more organic polar solvents, or a mixture of water and one or more of such solvents. Useful polar organic solvents include, but are not limited to, alcohols (such as isopropanol), alkyl acetates (such as ethyl acetate and propyl acetate), tetrahydrofuran and acetonitrile. Particularly useful polar organic solvents include isopropanol, ethyl acetate, propyl acetate, or mixtures or two or more of these. Isopropanol is most preferred.

Within the reaction mixture is one or more inorganic bases or formate salts. Many water-soluble inorganic salts are useful for this purpose, but more useful inorganic bases include, but are not limited to, carbonates, bicarbonates, borates and phosphates. Alkali metal, ammonium and trialkylammonium carbonates and bicarbonates are more preferred, and the ammonium, sodium and potassium carbonates are most preferred. The alkyl portions of the trialkylammonium cations generally have from 1 to 4 carbon atoms.

Useful formate salts include the alkali metal, ammonium and trialkylammonium salts (wherein the alkyl portions of the cations have from 1 to 4 carbon atoms). The ammonium, sodium and potassium salts are most preferred.

The amount of inorganic base or formate salt in the reaction medium is generally at least 0.25 molar equivalents, preferably at least 0.5 molar equivalents, based on the concentration of the reactants of Structure I in the medium. The amount can be generally up to 4 molar equivalents, preferably up to 2 molar equivalents, and more preferably up to 1.5 molar equivalents, based on the concentration of the reactants of Structure I in the medium.

The compounds of Structure I and the aromatic amines are generally present initially in the reaction mixture at a 1:1 stoichiometric ratio, although an excess of one or the other reactant can also be used if desired.

If the compounds of Structure II are to be further reacted to provide useful photographic dye forming coupler compounds, various known reactions can be used, including but not limited to, acylation (reaction with acid chloride), sulfonylation (reaction with a sulfonyl chloride), or isocyanation (reaction with an isocyanate) in suitable positions on the molecules. Details of some useful reactions are provided, U.S. Pat. No. 5,565,572 (noted above) and EP-A-0 779,543 (noted above), both incorporated herein by reference with regard to such reaction methods.

The following examples illustrate the practice of this invention which is not to be limited thereby.

EXAMPLE 1

COMPARATIVE REACTIONS TO FORM INTERMEDIATES

TABLE IV below shows the results for the reactions of Structure I compound CP-1 with aromatic amine AS-1 using either no base, an organic base (several are listed), an inorganic base (several are listed), or a formate salt in the reaction media. For all the reactions shown TABLE IV, where an organic or inorganic base or formate was used, two equivalents of base or formate were used. Included in the table are the reaction time, the high pressure liquid chromatography (HPLC) area % of the product formed (a measure of the degree to which the reaction goes to completion), the HPLC area % of unreacted CP-1, and the % isolated "Yield" of the resulting product intermediate. The reaction in which no organic or inorganic base was utilized, the reaction was carried out in tetrahydrofuran at reflux. All other reactions were carried out at 45° C. in isopropanol.

It can be seen from TABLE IV that when no base was present (Reaction 1), the reaction time was quite lengthy and the isolated yield was only moderate, even though the percent conversion to product was good. The isolation was not efficient because of impurities generated during the long reaction time. The reaction using the organic base triethylamine (Reaction 2) was shorter, but it also suffered from lower yields due to impurities generated during the reaction.

The uses of other organic bases (Reactions 3–6) were not effective in providing the desired products.

In contrast, the method of the invention (Reactions 7–11) all provided high yields to desired products.

Where reactant AS-1 was used (Reactions 1–7), it can be seen that the invention (Reactions 1–3) provided higher yields at shorter reaction times. Reactions 8–10 show the results for the use of amine compound AS-2. Reaction 8

TABLE IV

| Reaction | | Base | Reaction Time (hours) | Area % Product | Area % CP-1 | Yield |
|---|---|---|---|---|---|---|
| 1 | Comparison | — | 24 | 87.4 | 1.5 | 74.3 |
| 2 | Comparison | TEA | 6 | 86.4 | 0.6 | 71.0 |
| 3 | Comparison | DBU | 6 | 38.9 | 0.0 | — |
| 4 | Comparison | TMG | 4 | 28.0 | 0.0 | — |
| 5 | Comparison | DMA | 24 | 26.7 | 18.1 | — |
| 6 | Comparison | Pyr | 24 | 38.9 | 14.7 | — |
| 7 | Invention | $K_2CO_3$ | 2 | 90.3 | 0.4 | 80.6 |
| 8 | Invention | $(NH_4)HCOO$ | 22 | 82.2 | 2.7 | 80.3 |
| 9 | Invention | 1:1 AF:AC | 6 | 86.4 | 0.7 | 83.9 |
| 10 | Invention | $(NH_4)_2CO_3$ | 4 | 87.6 | 0.0 | 85.5 |
| 11 | Invention | $(NH_4)HCO_3$ | 6 | 88.3 | 0.4 | 83.9 |

TEA = triethylamine.
DBU = 1,8-Diazabicyclo[5.4.0]undec-7-ene.
TMG = 1,1,3,3-tetramethylguanidine.
DMA = N,N-dimethylaniline.
Pyr = pyridine.
AF = ammonium formate.
AC = ammonium carbonate.

EXAMPLE 2

PREPARATION USING VARIOUS AMINE REACTANTS

TABLE V below lists the results for various reactions of Structure I compound CP-1 with different amine reactants in the presence of no base, organic base triethylamine, an inorganic base, or a formate salt in the reaction medium. Where an organic or inorganic base or formate was used, it was present at one equivalent. Where no base or formate was present, the reaction was carried out at reflux in tetrahydrofuran. The other reactions were carried out at 45° C. in isopropanol.

represents the practice of the invention and provided the highest yield and the shortest reaction time. When AS-2 was used, no product was obtained in the absence of a base and very low yield was obtained from the reaction when the base was triethylamine (Reactions 9–10).

For Reactions 12–13 utilizing amine compound AS-3, no product was obtained wherein no base or only organic base was present. However, the same reactants in the presence of formate provided some desired product (Reaction 11). In Reactions 14–15, using amine compound AS-4, a significantly higher yield was obtained in a shorter reaction time with use of the present invention.

TABLE V

| Reaction | | Amine Compound | Base | Reaction Time (hours) | Area % Product | Area % CP-1 | Yield |
|---|---|---|---|---|---|---|---|
| 1 | Invention | AS-1 | $(NH_4)_2CO_3$ | 4 | 92.2 | 0.9 | 84.0 |
| 2 | Invention | AS-1 | $K_2CO_3$ | 4 | 90.8 | 0.2 | 90.3 |
| 3 | Invention | AS-1 | $(NH_4)HCO_3$ | 6 | 82.5 | 4.0 | 77.4 |
| 4 | Comparison | AS-1 | TEA | 6 | 84.8 | 0.1 | 72.0 |
| 5 | Comparison | AS-1 | TEA | 6 | 86.1 | 0.0 | 78.0 |
| 6 | Comparison | AS-1 | — | 24 | 87.4 | 1.5 | 74.3 |
| 7 | Comparison | AS-1 | — | 24 | 87.9 | 0.9 | 56.3 |
| 8 | Invention | AS-2 | $(NH_4)_2CO_3$ | 2 | 73.8 | 0.1 | 60.1 |
| 9 | Comparison | AS-2 | TEA | 4 | 61.3 | 0.8 | 21.9 |
| 10 | Comparison | AS-2 | — | 24 | 0.0 | 33.5 | — |
| 11 | Invention | AS-3 | $(NH_4)HCOO$ | 24 | 16.2 | 0.1 | — |
| 12 | Comparison | AS-3 | TEA | 24 | 0.4 | 0.1 | — |
| 13 | Comparison | AS-3 | — | 24 | 0.0 | 23.9 | — |
| 14 | Invention | AS-4 | $(NH_4)_2CO_3$ | 6 | 69.7 | 0.0 | 58.1 |
| 15 | Comparison | AS-4 | TEA | 24 | 37.6 | 0.0 | 25.0 |

23

In the following examples of the invention, all product compounds were characterized by spectral methods including mass spectroscopy and nuclear magnetic resonance. HPLC analysis was used to determine the purity of the isolated compounds as well as to monitor the progress of the reactions.

EXAMPLE 3

PREPARATION OF COMPOUND OF COMPOUND P-1

To a stirred solution of CP-1 (1.20 g, 5.0 mmol) in isopropanol (50 ml) was added AS-1 (2.20 g, 5.0 mmol) and ammonium carbonate (0.47 g, 5.0 mmol). The mixture was heated to 45° C. for 6 hours (HPLC analysis of an aliquot worked-up after 4 hours showed the reaction was done then). The mixture was cooled to room temperature, diluted with ethyl acetate (150 ml) and washed twice with 5% HCl (150 ml), twice with water (150 ml), and twice with brine (150 ml). The organic layer was then dried over magnesium sulfate and concentrated under reduced pressure. The resulting brown oil was recrystallized from ethyl acetate:heptane (1:7) to yield 2.60 g (84.0%) of an off-white solid. $MH^+=623$.

EXAMPLE 4

ALTERNATIVE SYNTHESIS OF COMPOUND P-1

Example 3 was followed except that ammonium bicarbonate (0.40 g, 5.0 mmol) was used in place of ammonium carbonate. The resulting brown oil was recrystallized from ethyl acetate:heptane (1:7) to yield 2.40 g (77.4%) of an off-white solid. $MH^+=623$.

EXAMPLE 5

STILL ANOTHER ALTERNATIVE SYNTHESIS OF COMPOUND P-1

Example 3 was followed except that potassium carbonate (0.69 g, 5.0 mmol) was used in place of ammonium carbonate, and dilution of the reaction product was carried out using 300 ml of ethyl acetate. The resulting brown oil was recrystallized from ethyl acetate:heptane (1:7) to obtain 2.80 g (90.3%) of an off-white solid. $MH^+=623$.

EXAMPLE 6

PREPARATION OF COMPOUND P-2

To a stirred solution of CP-1 (2.45 g, 10.0 mmol) in isopropanol (50 ml) was added AS-2 (3.72 g, 10.0 mmol) and ammonium carbonate (0.96 g, 10.0 mmol). The mixture was heated to 50° C. for 6 hours (HPLC of an aliquot taken after 2 hours showed the reaction was complete then). The mixture was cooled to room temperature, diluted with propyl acetate (150 ml) and washed three times with water (150 ml). The organic layer was then dried over magnesium sulfate and concentrated under reduced pressure. The resulting oil was purified by column chromatography on silica with 1:4 ethyl acetate:heptane to obtain 3.15 g (60.1 %) of an oil. All spectra were consistent with proposed structure.

EXAMPLE 7

PREPARATION OF COMPOUND P-4

To a stirred solution of CP-1 (2.45 g, 10.0 mmol) in isopropanol (50 ml) was added AS-4 (4.06 g, 10.0 mmol) and ammonium carbonate (0.96 g, 10.0 mmol). The mixture was heated to 50° C. for 6 hours. The mixture was cooled to room temperature, diluted with propyl acetate (150 ml) and three times with water (150 ml). The organic layer was then dried over magnesium sulfate and concentrated under reduced pressure. The resulting product was purified by column chromatography on silica. All spectra were consistent with proposed structure.

EXAMPLE 8

PREPARATION OF COMPOUND P-5

To a stirred solution of CP-1 (44.2 g, 0.182 mol) in isopropanol (400 ml) was added AS-9 (methyl m-aminobenzoate) (27.6 g, 0.182 mol) and ammonium formate (17.2 g, 0.273 mol). The mixture was heated to 50° C. overnight. The mixture was cooled to room temperature, diluted with ethyl acetate (500 ml) and washed with water (300 ml). The organic layer was then dried over magnesium sulfate and concentrated under reduced pressure. The resulting brown oil dissolved in 200 ml of dichloromethane and concentrated again to get a tan/pinkish colored solid. This solid was then purified by trituration with toluene to yield 51 g (83%) of P-5. M/e=332, MP=166–168° C.

EXAMPLE 9

PREPARATION OF COMPOUND P-6

To a stirred solution of CP-3 (50.0 g, 0.176 mol) in isopropanol (250 ml) was added AS-9 (methyl m-aminobenzoate) (24.9 g, 0.165 mol) and ammonium carbonate (16.9 g, 0.176 mol). The mixture was heated to 45° C. for 3 hours. TLC (20% ethyl acetate, 80% heptane) showed the reaction was complete. The reaction was stirred at room temperature overnight for convenience. The mixture was diluted with ethyl acetate (250 ml) and washed with water (250 ml). The aqueous layer was removed, and a solid remained floating in the organic layer. The organic layer with the solid present was washed with 5% HCl (250 ml), and then washed with brine (250 ml). The solid was removed by filtration. The filtrate was concentrated under reduced pressure to give a solid. This solid was triturated with methylene chloride, and the slurry was held at 5° C. overnight. The solid was collected by filtration and added to the first yield to give a total of 55.0 g (83%) of Compound P-6 as an off-white solid. All spectra were consistent with proposed structure.

The invention has been described in detail with particular reference to certain preferred embodiments thereof, but it will be understood that variations and modifications can be effected within the spirit and scope of the invention.

We claim:

1. A method for preparing a pyrazolotriazole dye forming coupler compound or coupler intermediate compound comprising inducing an elimination-addition reaction between an aromatic amine and a compound having Structure I in the presence of an inorganic base, a formate salt or both,

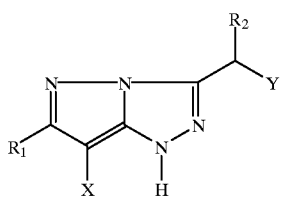

I wherein $R_1$ is an alkyl, aryl, alkoxy, aryloxy, acyl or amido group, $R_2$ is hydrogen or an alkyl or aryl group, X is hydrogen or a coupling-off group and Y is a leaving group that is capable of being replaced in an elimination-addition reaction.

2. The method of claim 1 wherein said inorganic base is a carbonate, bicarbonate, borate or phosphate.

3. The method of claim 1 wherein said inorganic base is a carbonate or bicarbonate.

4. The method of claim 1 carried out at a temperature of from about 25 to about 65° C.

5. The method of claim 1 wherein said aromatic amine is represented by $NH(R_3)R_4$ wherein at least one of $R_3$ and $R_4$ is an aromatic group, and the other is hydrogen, an alkyl group or an aryl group.

6. The method of claim 5 wherein $R_3$ is an aryl group and $R_4$ is hydrogen or an alkyl group.

7. The method of claim 6 wherein $R_3$ is a phenyl group and $R_4$ is hydrogen.

8. The method of claim 1 wherein $R_1$ is an alkyl, aryl, amido, alkoxy or aryloxy group, $R_2$ is an alkyl or aryl group, X is hydrogen, halo, or an alkylthiol, arylthiol or phenoxy group, and Y is halo, or an aryloxy, acyloxy or alkoxy group.

9. The method of claim 8 wherein $R_1$ is an alkyl, phenyl or phenoxy group, $R_2$ is a phenyl or alkyl group, X is hydrogen, chloro, phenoxy or carboethoxyethylthio, and Y is halo, or a p-nitrophenoxy or acetoxy group.

10. The method of claim 1 wherein said inorganic base or formate salt is present in an amount of from about 0.25 to 4 molar equivalents based on the concentration of the compound of Structure I.

11. The method of claim 1 wherein said compound of Structure I is

CP-1
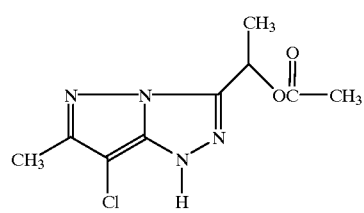

CP-2
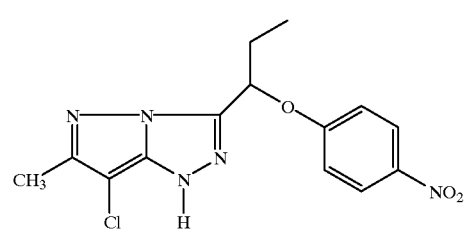

CP-3
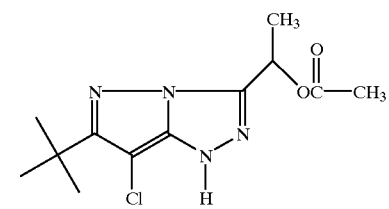

CP-4
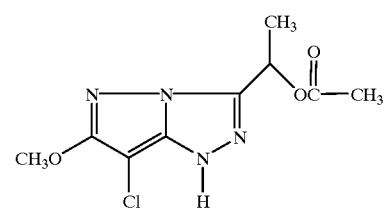

CP-5
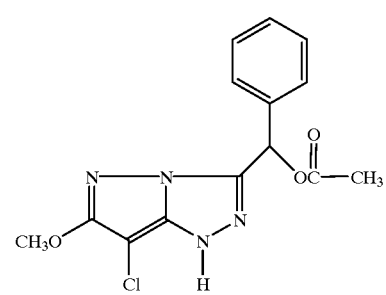

CP-6
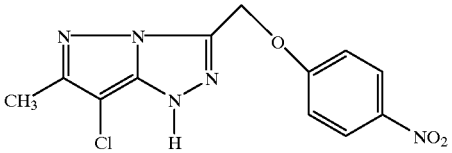

CP-7
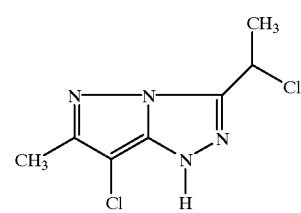

CP-8
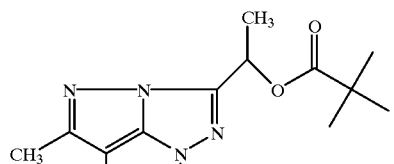

CP-9
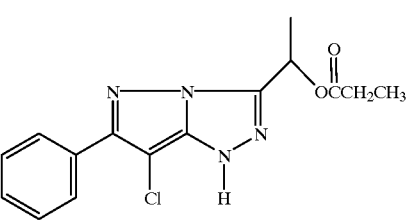

CP-10
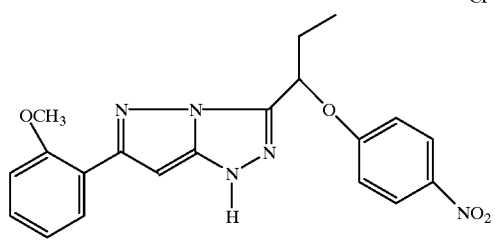
CP-11
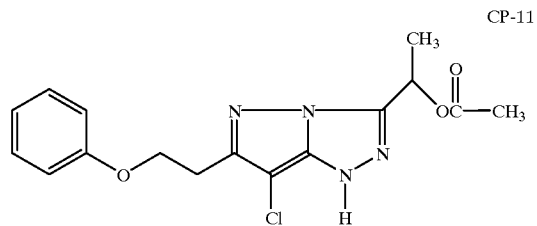
CP-12
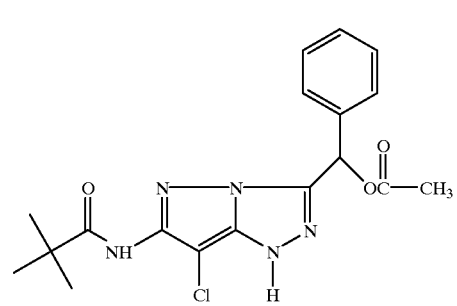
CP-13
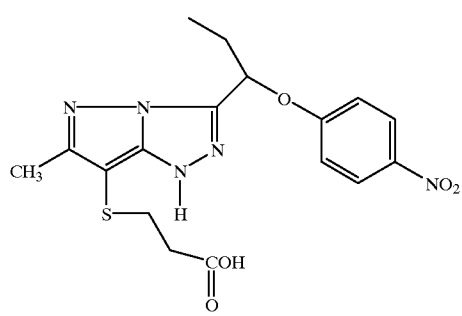
CP-14
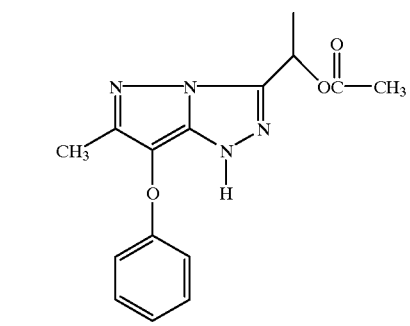
CP-15
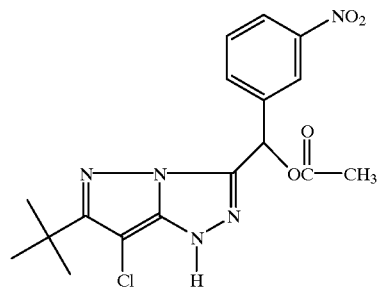
CP-16
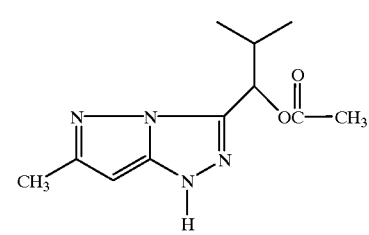
CP-17
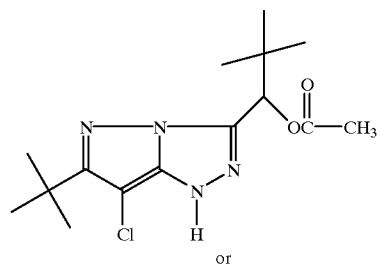
or
CP-18
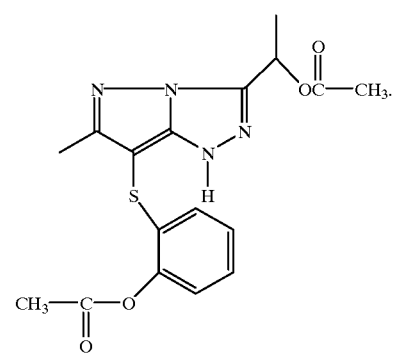
12. The method of claim 1 wherein said aromatic amine is
AS-1
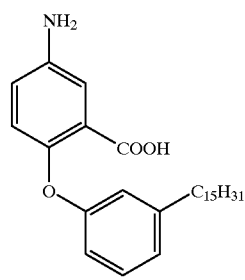

-continued
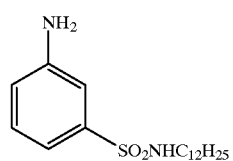 AS-2
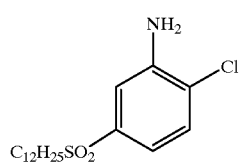 AS-3
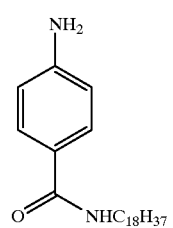 AS-4
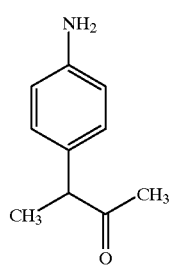 AS-5
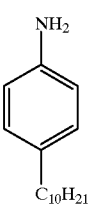 AS-6
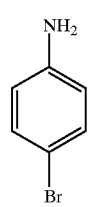 AS-7
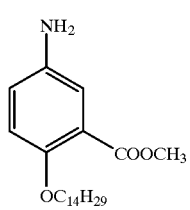 AS-8
-continued
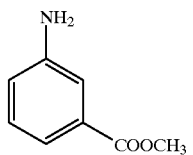 AS-9
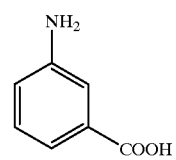 AS-10
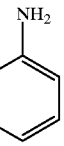 AS-11
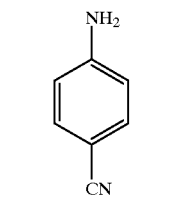 AS-12
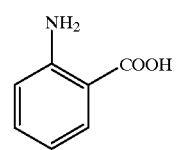 AS-13
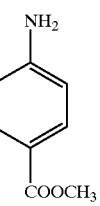 AS-14
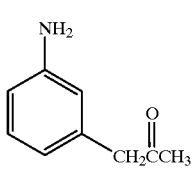 AS-15
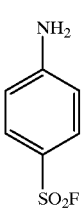 AS-16

AS-17
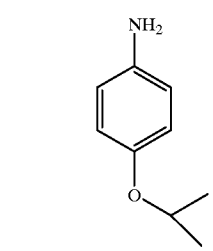
AS-18
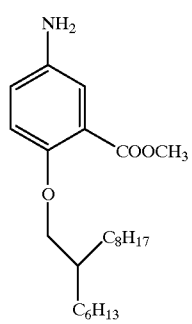
AS-19
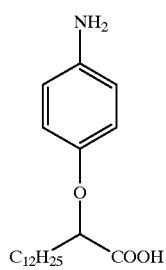
AS-20
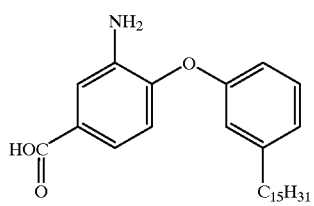
AS-21
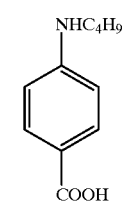
AS-22
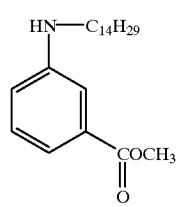
AS-23
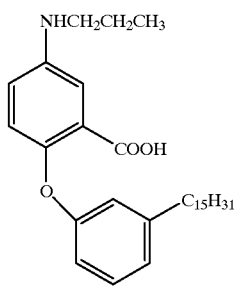
AS-24
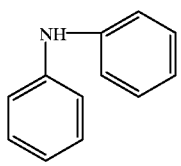
AS-25
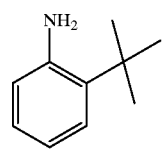
AS-26
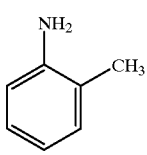
AS-27
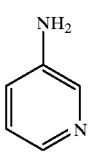
AS-28
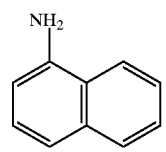
AS-29
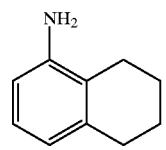
AS-30
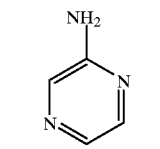
AS-31
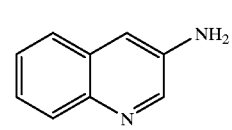

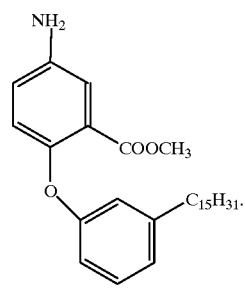

AS-32

13. A method of preparing a pyrazolotriazole dye forming coupler compound comprising:

A) inducing an elimination-addition reaction between an aromatic amine with a compound having Structure I in the presence of an inorganic base, a formate salt or both,

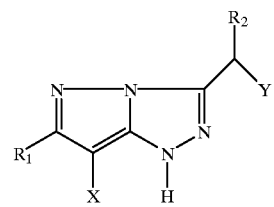

wherein $R_1$ is an alkyl, aryl, alkoxy, aryloxy, acyl or amido group, $R_2$ is hydrogen or an alkyl or aryl group, X is hydrogen or a coupling-off group and Y is a leaving group that is capable of being replaced in an elimination-addition, B) further reacting the product obtained in step A.

* * * * *